(12) United States Patent
Okamoto et al.

(10) Patent No.: US 8,987,532 B2
(45) Date of Patent: Mar. 24, 2015

(54) PROCESS FOR PRODUCING 1,2-DICHLORO-3,3,3-TRIFLUOROPROPENE

(71) Applicant: Central Glass Company, Limited, Ube-shi, Yamaguchi (JP)

(72) Inventors: Satoru Okamoto, Kawagoe (JP); Yoshio Nishiguchi, Kawagoe (JP); Fuyuhiko Sakyu, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 14/242,309

(22) Filed: Apr. 1, 2014

(65) Prior Publication Data

US 2014/0357907 A1    Dec. 4, 2014

(30) Foreign Application Priority Data

Apr. 2, 2013  (JP) ................................. 2013-076737
Mar. 20, 2014  (JP) ................................. 2014-058633

(51) Int. Cl.
*C07C 17/04*        (2006.01)

(52) U.S. Cl.
CPC ..................................... *C07C 17/04* (2013.01)
USPC .......................... 570/153; 570/156; 570/170

(58) Field of Classification Search
USPC ......................................... 570/153, 156, 170
See application file for complete search history.

(56) References Cited

U.S. PATENT DOCUMENTS 8,754,273 B2 *  6/2014  Zhai et al. .................... 570/170

FOREIGN PATENT DOCUMENTS

JP         2012-20992 A      2/2012
WO    WO 2013/085770    *   6/2013

OTHER PUBLICATIONS

Henne et al., "A New Method of Synthesizing Organic 1,1,1-Trifluorides," J. Am. Chem. Soc., 1941, vol. 63, pp. 3478-3479.
Whaley et al., "Isomerization During Allylic Fluroination," J. Am. Chem. Soc., 1948, vol. 70, pp. 1026-1027.
Haszeldine, "Reactions of Flurocarbon Radicals. Part V.* Alternative Syntheses for Trifluoromethylacetylene (3:3:3-Trifluoropropene), and the Influence of Polyfluoro-groups on Adjacent Hydrogen and Halogen Atoms," J. Am. Chem. Soc., 1951, pp. 2495-2504.

* cited by examiner

*Primary Examiner* — Shailendra Kumar
(74) *Attorney, Agent, or Firm* — Crowell & Moring LLP

(57) ABSTRACT

Disclosed is a process for producing 1,2-dichloro-3,3,3-trifluoropropene, which is characterized by that 1-halogeno-3,3,3-trifluoropropene represented by the general formula [1]:

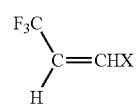

[1]

(In the formula, X represents a fluorine atom, chlorine atom or bromine atom.) is reacted with chlorine in a gas phase in the presence of a catalyst. It is possible by this process to produce 1,2-dichloro-3,3,3-trifluoropropene in an industrial scale with good yield by using 1-halogeno-3,3,3-trifluoropropene, which is available with a low price, as the raw material.

15 Claims, No Drawings

PROCESS FOR PRODUCING 1,2-DICHLORO-3,3,3-TRIFLUOROPROPENE

TECHNICAL FIELD

The present invention relates to a process for producing 1,2-dichloro-3,3,3-trifluoropropene.

BACKGROUND TECHNIQUES

Various processes are known as the process for producing 1,2-dichloro-3,3,3-trifluoropropene (HCFC-1223xd). For example, Non-patent Publication 1 discloses a process for conducting a liquid-phase reaction of 1,2,3,3,3-pentachloropropene with antimony trifluoride.

Furthermore, Non-patent Publication 2 discloses a process of reacting 1,1,2,3,3-pentachloropropene with antimony trifluoride in a liquid phase with the addition of antimony pentachloride. Non-patent Publication 3 discloses a production process in which potassium hydroxide in the form of solid is added to 1,2,2-trichloro-3,3,3-trifluoropropane of liquid, followed by a reflux operation with heating.

As a gas-phase reaction, in Patent Publication 1, there is disclosed a process for producing a fluorine-containing propene represented by the general formula CF$_3$CH=CHZ (Z is Cl or F.) by a fluorination reaction and a dehalogenation reaction, using a chlorine-containing compound as the raw material. In its Example 4, there is a description that 1,2-dichloro-3,3,3-trifluoropropene is produced as a by-product of a fluorination reaction and a dehalogenation reaction of 1,1,1,3,3-pentachloropropane (HCC-240fa).

PRIOR ART PUBLICATIONS

Patent Publications

Patent Publication 1: Japanese Patent Application Publication 2012-20992

Non-Patent Publications

Non-patent Publication 1: A. L. Henne et al., J. Am. Chem. Soc., 1941, p. 3478-3479
Non-patent Publication 2: A. M. Whaley et al., J. Am. Chem. Soc., 1948, p. 1026-1027
Non-patent Publication 3: R. N. Haszeldine, J. Chem. Soc., 1951, p. 2495-2504

SUMMARY OF THE INVENTION

In the production process described in Non-patent Publication 3, the reaction is conducted by dispersing potassium hydroxide in the form of powder in 1,2,2-trichloro-3,3,3-trifluoropropane in the form of liquid, but yield is low (48%), and it is a heterogeneous reaction. Therefore, it has been difficult to say efficient in terms of an industrial production process.

Furthermore, as described in Patent Publication 1, it is known that, in a gas phase, 1,2-dichloro-3,3,3-trifluoropropene is produced by a fluorination reaction and a dehalogenation reaction of a chlorine-containing compound such as 1,1,1,3,3-pentachloropropane. It is, however, difficult to obtain 1,2-dichloro-3,3,3-trifluoropropene in an industrially sufficient amount.

As mentioned above, there has been a demand for establishing a process for producing 1,2-dichloro-3,3,3-trifluoropropene as the target of the present invention in an industrial scale.

Thus, it is an object of the present invention to provide a process for producing 1,2-dichloro-3,3,3-trifluoropropene, which can be implemented in an industrial scale, in a gas phase reaction.

It is known that olefins having a carbon double bond easily undergo an addition reaction with a halogen, since the double bond moiety is chemically active. Based on this finding, when 1-chloro-3,3,3-trifluoropropene (HCFC-1233zd) as one of olefins was reacted with chlorine in a liquid phase, an addition reaction of chlorine progressed, thereby producing 1,1,2-trichloro-3,3,3-trifluoropropane (HCFC-233da) resulting from adding chlorine atoms to the double bond moiety (see Scheme 1 and Reference Example 1).

<Scheme 1>

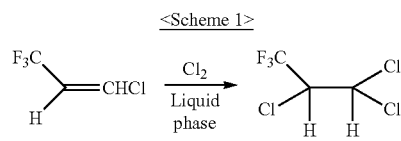

The prevent inventors, however, have found that, when 1-halogeno-3,3,3-trifluoropropene represented by the general formula [1]:

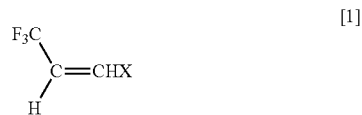

[1]

(In the formula, X represents a fluorine atom, chlorine atom or bromine atom.) is reacted with chlorine in a gas phase in the presence of a catalyst, unlike the halogen addition reaction in a liquid phase, it is possible to obtain a compound resulting from selectively converting a part of hydrogen atoms of 1-halogeno-3,3,3-trifluoropropene to a chlorine atom, that is, 1,2-dichloro-3,3,3-trifluoropropene (HCFC-1223xd), with a high yield, thereby reaching the present invention. The reaction mechanism is not certain, but this compound is assumed to have been obtained by that a reaction intermediate obtained by adding chlorine to the double bond moiety immediately underwent a dehydrohalogenation (See Scheme 2. Starting material: 1-chloro-3,3,3-trifluoropropene).

<Scheme 2>

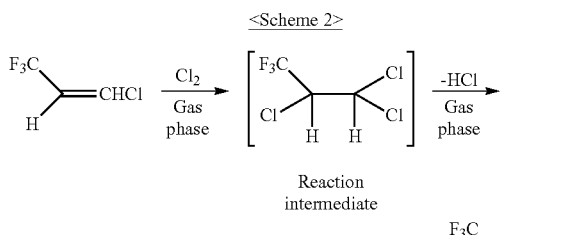

Reaction intermediate

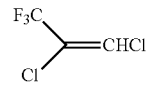

The present invention includes the following Inventions 1-18.

[Invention 1]

A process for producing 1,2-dichloro-3,3,3-trifluoropropene, which is characterized by that 1-halogeno-3,3,3-trifluoropropene represented by the general formula [1]:

$$\underset{H}{\overset{F_3C}{>}}C=CHX \qquad [1]$$

(In the formula, X represents a fluorine atom, chlorine atom or bromine atom.) is reacted with chlorine in a gas phase in the presence of a catalyst.

[Invention 2]

The production process of Invention 1, wherein the 1-halogeno-3,3,3-trifluoropropene and the chlorine are brought into contact with the catalyst with a contact time of from 1 second to 300 seconds at a reaction temperature of from 100° C. to 350° C.

[Invention 3]

The production process of Invention 1 or 2, wherein the 1-halogeno-3,3,3-trifluoropropene is 1-chloro-3,3,3-trifluoropropene.

[Invention 4]

The production process of any one of Inventions 1-3, wherein the catalyst is a metal compound containing at least one metal selected from the group consisting of aluminum, chromium, titanium, manganese, iron, nickel, cobalt, copper, magnesium, zirconium, molybdenum, zinc, tin, lanthanum, and antimony.

[Invention 5]

The production process of Invention 4, wherein the metal compound is a metal fluoride.

[Invention 6]

The production process of Invention 4 or 5, wherein the metal compound is a fluorinated alumina or a fluorinated chromia.

[Invention 7]

The production process of any one of Inventions 1-3, wherein the catalyst is a supported catalyst in which a metal compound containing at least one metal selected from the group consisting of aluminum, chromium, titanium, manganese, iron, nickel, cobalt, copper, magnesium, zirconium, molybdenum, zinc, tin, lanthanum, and antimony is supported on carbon.

[Invention 8]

The production process of Invention 7, wherein the metal compound is a metal fluoride.

[Invention 9]

The production process of Invention 7, wherein the catalyst is an antimony-supported activated carbon or a chromium-supported activated carbon.

[Invention 10]

The production process of any one of Inventions 1-3, wherein the catalyst is activated carbon.

[Invention 11]

A process for producing a high-purity 1,2-dichloro-3,3,3-trifluoropropene, which is characterized by that the 1,2-dichloro-3,3,3-trifluoropropene obtained by the production process of any one of inventions 1-10 is further purified.

[Invention 12]

A process for producing 1,2-dichloro-3,3,3-trifluoropropene, which is characterized by that 1-halogeno-3,3,3-trifluoropropene separated from the 1,2-dichloro-3,3,3-trifluoropropene by the production process of Invention 11 is recovered.

[Invention 13]

A process for producing 1,2-dichloro-3,3,3-trifluoropropene, which is characterized by that 1-halogeno-3,3,3-trifluoropropene separated from the 1,2-dichloro-3,3,3-trifluoropropene by the production process of Invention 11 is used again as the raw material.

[Invention 14]

A process for producing trans-1,2-dichloro-3,3,3-trifluoropropene, which is characterized by that the 1,2-dichloro-3,3,3-trifluoropropene obtained by the production process of any one of Inventions 1-13 is further purified.

[Invention 15]

A process for producing cis-1,2-dichloro-3,3,3-trifluoropropene, which is characterized by that the 1,2-dichloro-3,3,3-trifluoropropene obtained by the production process of any one of Inventions 1-13 is further purified.

Advantageous Effect of the Invention

According to the present invention, it is possible to efficiently produce 1,2-dichloro-3,3,3-trifluoropropene by continuously conducting reactions of chlorination and dehydrohalogenation by a single reaction step using 1-halogeno-3,3,3-trifluoropropene, which is easily available, as the raw material. Therefore, according to the present invention, it is possible to obtain 1,2-dichloro-3,3,3-trifluoropropene in an industrial scale by a process with an easy implementation.

DETAILED DESCRIPTION

The reaction according to the present invention is a process for producing 1,2-dichloro-3,3,3-trifluoropropene, which is characterized by that 1-halogeno-3,3,3-trifluoropropene is reacted with chlorine in a gas phase in the presence of a catalyst. The process of the present invention is characterized by that it is possible to continuously conduct reactions of chlorination and dehydrohalogenation by a single reaction step of conducting the reaction with chlorine in a gas phase in the presence of a catalyst (see Scheme 2).

Specifically, a reactor is charged with a catalyst, and at a predetermined temperature 1-halogeno-3,3,3-trifluoropropene and chlorine are brought into contact with the catalyst in a gas phase. With this, it is possible to obtain a reaction product containing 1,2-dichloro-3,3,3-trifluoropropene. By further purifying the reaction product, it is possible to obtain a high-purity 1,2-dichloro-3,3,3-trifluoropropene. The treatment mode may be flow mode or batch mode. Since chemical substances involved in the reaction have low boiling points, flow mode is preferable in practice. In a gas-phase flow mode, the method for retaining the catalyst may be any mode, such as a fixed bed type, a fluidized bed type, and a moving bed. Conducting that with a fixed bed type is simple and easy. Therefore, it is preferable.

We explain 1-halogeno-3,3,3-trifluoropropene represented by the formula [1] used as the starting raw material of the present invention. As X in 1-halogeno-3,3,3-trifluoropropene, specifically a fluorine atom, chlorine atom or bromine atom is cited. As specific compounds of 1-halogeno-3,3,3-trifluoropropene, it is possible to cite 1,3,3,3-tetrafluoropropene (1234ze), 1-chloro-3,3,3-trifluoropropene (1233zd), and 1-bromo-3,3,3-trifluoropropene. In the case of using 1,3,3,3-tetrafluoropropene in the present invention, if a chlorine source exists in the reaction system, it results in 1-chloro-3,3,3-trifluoropropene, which is thermodynamically stable, and finally it is possible to obtain 1,2-dichloro-3,3,3-trifluoropropene.

Of these, due to easy availability and usefulness of the compound to be obtained, 1-chloro-3,3,3-trifluoropropene is preferably used.

Since 1-halogeno-3,3,3-trifluoropropene is produced in an industrial scale, it can be purchased for its use. For example, 1-chloro-3,3,3-trifluoropropene can be obtained by the methods described in Japanese Patent Application Publication Heisei 9-194404 and Japanese Patent Application Publication Heisei 10-067693.

The catalyst used in the present invention is not particularly limited, as long as it is capable of conducting a conversion to 1,2-dichloro-3,3,3-trifluoropropene by bringing 1-halogeno-3,3,3-trifluoropropene and chlorine into contact with the catalyst. As such one, it is possible to cite, for example, a metal-containing metal compound, activated carbon, etc. The catalyst may be either an unsupported catalyst or a supported catalyst. In the following, the catalyst of the present invention is explained in detail.

As the unsupported catalyst, a metal-containing metal fluoride and activated carbon are preferable. The metal contained in the catalyst is at least one metal selected from the group consisting of aluminum, chromium, titanium, manganese, iron, nickel, cobalt, copper, magnesium, zirconium, molybdenum, zinc, tin, lanthanum, and antimony. It may be used singly or as a composite metal in which at least two metals are in a complex. Metal fluorides containing these metals are obtained by conducting a fluorination treatment on metal oxides prepared by oxidizing these metals. In the present specification, "metal fluoride" refers to one prepared by partially or completely replacing oxygen atoms of the metal oxide with fluorine atoms. The metal oxide used as a material upon obtaining a metal fluoride may have different crystal systems, but any of those can be used. For example, as alumina, γ-alumina is preferable due to its large surface area.

As the composite metal, those are preferable, which contain, as a major component, aluminum, chromium, titanium, manganese, iron, nickel, cobalt, copper, magnesium, zirconium, molybdenum, zinc, tin, lanthanum and antimony, and, as a minor component, aluminum, chromium, titanium, manganese, iron, nickel, cobalt, copper, magnesium, zirconium, molybdenum, zinc, tin, lanthanum, antimony, etc.

As such composite metal, it is possible to cite oxides of composite metals of aluminum and chromium, aluminum and zirconium, aluminum and titanium, and aluminum and magnesium, as preferable ones. More specifically, it is possible to cite alumina and chromia, alumina and zirconia, alumina and titania, and alumina and magnesia, as preferable ones. These oxides of composite metal are preferably ones each containing at least 50 atomic % of aluminum, more preferably ones each containing at least 80 atomic % of aluminum.

The metal oxide used as the material of the metal fluoride may take a plurality of crystal forms. For example, alumina may have crystal forms of γ-alumina and α-alumina, and titania may have crystal forms of anatase and rutile. Any crystal form of the metal oxide will do. In the case of alumina, however, γ-alumina is preferable due to its large surface area.

In the reaction of the present invention, a metal fluoride or activated carbon is used as the catalyst. In the case of using a metal oxide not fluorinated, 1-halogeno-3,3,3-trifluoropropene acts as a fluorinating agent. Therefore, the metal oxide is converted to a metal fluoride with the passage of time, thereby causing a tendency for the reaction to become not stable. Therefore, as the catalyst, there is preferable a metal fluoride prepared by previously conducting a fluorination treatment on the metal oxide. In a metal fluoride produced by conducting a fluorination treatment on the metal oxide, the ratio of the replacement of oxygen atoms with fluorine atoms is not particularly limited, but one with a wide range is usable. Herein, it is possible to use not only a metal fluoride prepared by replacing all of oxygen atoms of the metal oxide with fluorine atoms, but also a metal fluoride prepared by partially replacing oxygen atoms of the metal oxide with fluorine atoms.

The preparation of the metal fluoride is conducted by bring a fluorinating agent, such as hydrogen fluoride, a fluorinated hydrocarbon and a fluorochlorinated hydrocarbon, and the above-mentioned metal oxide or oxide of composite metal into contact with each other. Normally, it is preferable to conduct the fluorination treatment in a stepwise manner. In the case of conducting the fluorination treatment with hydrogen fluoride, it is accompanied with a severe heat generation. Therefore, it is preferable to firstly fluorinate the metal oxide at a relatively low temperature by a diluted hydrofluoric acid aqueous solution or hydrogen fluoride gas and then conduct that while gradually increasing the concentration and/or temperature. At the final stage, it is preferable to conduct that at a temperature higher than the predetermined reaction temperature. In addition to this condition, in order to prevent the change with the passage of time in the reaction, it is preferable to conduct the fluorination treatment with hydrogen fluoride at a fluorination temperature of 200° C. or higher, 400° C. or higher, more preferably 500° C. or higher. The temperature does not have a particular upper limit. Exceeding 900° C. is difficult in terms of heat resistance of the fluorination treatment apparatus. In practice, it is preferable to conduct that at 600° C. or lower. As mentioned above, in order to prevent compositional change of the solid catalyst in the reaction, it is preferable to use, as the catalyst, a metal fluoride prepared by previously conducting a fluorination treatment on the metal oxide with a fluorinating agent, such as hydrogen fluoride, a fluorinated hydrocarbon, or a fluorochlorinated hydrocarbon, at a temperature higher than the predetermined reaction temperature, prior to the use.

As the unsupported catalyst, it is possible to use carbon, too. The carbon to be used is not particularly limited, but there are vegetable series activated carbons using raw materials such as wood, charcoal, coconut husk coal, palm core coal, and raw ash; coal series activated carbons using raw materials such as peat, lignite, brown coal, bituminous coal, and anthracite; petroleum series activated carbons using raw materials such as petroleum residue and oil carbon; or synthetic resin series activated carbons using raw materials such as carbonated polyvinylidene chloride. It is possible to use one by selecting from these commercial carbons. There are preferably used, for example, coconut husk coals for gas purification and for catalyst and catalyst support (GRANULAR SHIRO SAGI GX, SX, CX and XRC made by Japan Enviro-Chemicals, Ltd., PCB made by TOYO CALGON CO., YASHI-COAL made by Taihei Chemical Industrial Co., Ltd., and KURARAY-COAL GG and GC), etc.

Regarding the shape of carbon used as the unsupported catalyst, it is used generally in the form of granules, but it is also possible to use one in the form of sphere, fiber, powder or honeycomb in a normal setting condition range, as long as it fits into the reactor to be used. It is acceptable that the specific surface area and the micropore volume of the carbon are in ranges of the standard of commercial products. It is preferable that the specific surface area is greater than 400 m$^2$/g and that the micropore volume is greater than 0.1 cm$^3$/g. It is particularly preferable that the specific surface area is 800-3000 m$^2$/g and that the micropore volume is 0.2-1.0 cm$^3$/g.

In the present invention, it is optional to use a supported catalyst supporting a metal compound. As the support of the supported catalyst supporting a metal to be used in the present invention, it is optional to use carbon or the metal (including a composite metal containing at least two metals) mentioned above as the unsupported catalyst. The metal used as the support may be a metal oxide. It is optional to singly use, as the support, a metal oxide containing at least one metal selected from the group consisting of aluminum, chromium, titanium, manganese, iron, nickel, cobalt, copper, magnesium, zirconium, molybdenum, zinc, tin, lanthanum, and antimony. Alternatively, it is optional to use, as the support, a composite metal oxide in which at least two metals are in a complex. As the composite metal oxide, those are preferable, which contain, as a major component, oxides of aluminum, chromium, titanium, manganese, iron, nickel, cobalt, copper, magnesium, zirconium, molybdenum, zinc, tin, lanthanum and antimony, and, as a minor component, oxides of aluminum, chromium, titanium, manganese, iron, nickel, cobalt, copper, magnesium, zirconium, molybdenum, zinc, tin, lanthanum and antimony, etc.

In the case of using carbon as the support, the carbon support is not particularly limited. Specifically, it is possible to cite vegetable series activated carbons using raw materials such as wood, charcoal, coconut husk coal, palm core coal, and raw ash; coal series activated carbons using raw materials such as peat, lignite, brown coal, bituminous coal, and anthracite; petroleum series activated carbons using raw materials such as petroleum residue and oil carbon; or synthetic resin series activated carbons using raw materials such as carbonated polyvinylidene chloride. It is possible to use one by selecting from these commercial carbons. There are preferably used, for example, coconut husk coals for gas purification and for catalyst and catalyst support (GRANULAR SHIRO SAGI GX, SX, CX and XRC made by Japan Enviro-Chemicals, Ltd., PCB made by TOYO CALGON CO., YASHI-COAL made by Taihei Chemical Industrial Co., Ltd., and KURARAY-COAL GG and GC), etc.

Regarding the shape of carbon used as the support, it is used generally in the form of granules, but it is also possible to use one in the form of sphere, fiber, powder or honeycomb in a normal setting condition range, as long as it fits into the reactor to be used. It is acceptable that the specific surface area and the micropore volume of the carbon are in ranges of the standard of commercial products. It is preferable that the specific surface area is greater than 400 $m^2/g$ and that the micropore volume is greater than 0.1 $cm^3/g$. It is particularly preferable that the specific surface area is 800-3000 $m^2/g$ and that the micropore volume is 0.2-1.0 $cm^3/g$.

As the metal contained in the metal compound to be supported, it is possible to cite aluminum, chromium, titanium, manganese, iron, nickel, cobalt, copper, magnesium, zirconium, molybdenum, zinc, tin, lanthanum, antimony, etc. Of these, aluminum, chromium, titanium, zirconium, and antimony are preferable. These metals are supported as fluorides, chlorides, fluorochlorides, oxyfluorides, oxychlorides, oxyfluorochlorides, etc. At least two metal compounds together may be supported.

The percentage of mass of the metal relative to the total mass of the catalyst containing the support and the supported substance is 0.1-80 mass %, preferably 1-50 mass %. If it is less than 0.1 mass %, the catalyst effect is low. If it is greater than 80 mass %, a stable supporting is difficult. Therefore, both of these are not preferable. In case that the supported substance is a solid metal salt, the percentage of mass of the metal relative to the total mass of the catalyst is 0.1-40 mass %, preferably 1-30 mass %.

As the metal compound to be supported on the support, specifically, it is possible to use chromium nitrate, chromium trichloride, potassium dichromate, titanium trichloride, manganese nitrate, manganese chloride, ferric chloride, nickel nitrate, nickel chloride, cobalt nitrate, cobalt chloride, antimony pentachloride, magnesium chloride, magnesium nitrate, zirconium chloride, zirconium oxychloride, zirconium nitrate, copper (II) chloride, zinc (II) chloride, lanthanum nitrate, tin tetrachloride, etc.

In order to prevent the compositional change of the catalyst during the reaction, it is preferable by a method similar to the above-mentioned fluorination treatment of the metal oxide to previously conduct a treatment, prior to the use, on the catalyst prepared by supporting the above-mentioned metal compound on the support, with a fluorinating agent, such as hydrogen fluoride, fluorinated hydrocarbon, fluorochlorinated hydrocarbon, etc., at a temperature higher than the predetermined reaction temperature.

Herein, in case that the support is a metal oxide and that the support is entirely covered with a layer of the metal compound as the supported substance, in the fluorination treatment step, the support is not fluorinated, but only the supported substance is subjected to the fluorination treatment. In this case, even in the reaction, only the supported substance acts as a catalyst. However, in case that the support is a metal oxide and that the support is not entirely covered with a layer of the metal compound as the supported substance, not only the supported substance but also the support may be subjected to a fluorination treatment in the fluorination treatment step. Therefore, not only the supported substance but also the support may act as a catalyst in the reaction. In this manner, in case that not only the supported substance but also the support acts as a catalyst, it may act as a complex metal fluoride similar to the unsupported catalyst, not as the supported catalyst.

As the catalyst used in the present invention, it is possible to cite antimony-supported activated carbon, chromium-supported activated carbon, activated carbon, fluorinated alumina, and fluorinated chromia as its preferable specific examples. Antimony-supported activated carbon and chromium-supported activated carbon are particularly preferable. It is preferable to previously conduct a fluorination treatment on these catalysts, prior to the reaction. In the case of antimony-supported activated carbon, however, it is possible to obtain a stable reaction activity even if the fluorination treatment is not conducted. Furthermore, in the case of activated carbon as the unsupported catalyst too, it is possible to obtain the target product by activated carbon alone even if the fluorination treatment is not conducted (see Example 1).

The amount of chlorine supplied to the reaction region is normally 0.1-2.0 mol, preferably 0.5-1.2 mol, relative to 1 mol of 1-halogeno-3,3,3-trifluoropropene. If it is less than 0.1 mol, productivity of the target product is low. Therefore, it is not preferable. If it is greater than 2.0 mol, the production of perchlorinated products increases. Therefore, it is not preferable.

The temperature for conducting the reaction according to the present invention is normally 100° C. to 350° C., more preferably 150° C. to 300° C. If it is lower than 100° C., the reaction does almost not progress or is extremely slow. Therefore, it is not preferable. If it is higher than 350° C., there may occur a contamination with large amounts of by-products by the progress of decomposition reactions, perchlorination reactions, etc. Therefore, it is not preferable. As the by-products, it is possible to cite perchlorinated products, such as $CF_3CCl=CCl_2$ (1,1,2-trichloro-3,3,3-trifluoropropene: 1213xa), $CF_3CCl_2CCl_3$ (1,1,1,2,2-pentachloro-3,3,3-trifluoropropane: 213ab), etc.

If the reaction temperature is in a range of 100° C. to 350° C., it is possible to reduce the production of by-products in the reaction product according to the present invention. Furthermore, due to no production of by-products having boiling points close to that of 1,2-dichloro-3,3,3-trifluoropropene as the target product, it is possible to easily purify 1,2-dichloro- 3,3,3-trifluoropropene from the obtained reaction product by an operation such as distillation. To conduct the reaction within this temperature range is economically advantageous and small in terms of environmental load, too.

In the present specification, contact time of the reaction according to the present invention is defined as follows. That is, volume of the loading (catalyst) is represented by A. On the other hand, volume of the raw material gas introduced into the reactor per second is represented by B. The value of B is calculated from the number of moles of the raw material introduced per second, pressure and temperature, suppose that the raw material gas is an ideal gas. Upon this, the value (=A/B) determined by dividing A by B is defined as "contact time". In the reactor, gases other than the target product are produced as by-products to cause change in the number of moles, but these are not considered upon calculating "contact time".

Contact time depends on the temperature (reaction temperature) and the shape of the reactor used in the present invention and the type of the loading (catalyst). Therefore, it is desirable to suitably adjust the supply rate (contact time) of the reaction raw material to determine the optimum value for each of the predetermined temperature, the shape of the reactor, and the type of the loading (catalyst). Normally, from the viewpoints of recovery and reuse of the unreacted raw material, it is preferable to use a contact time with which a raw material conversion of 25% or greater can be obtained. More preferably, the contact time is optimized to obtain a conversion of 50% or greater.

In the reaction of the present invention, an appropriate combination of the reaction temperature and the contact time is an important factor. In case that the reaction temperature is from 100° C. to 350° C., the contact time is preferably made to be from one second to 300 seconds, more preferably from 20 seconds to 150 seconds. If the contact time exceeds 300 seconds, side reactions tend to occur. If the contact time is shorter than one second, conversion is low. Therefore, it is not preferable. It is one of preferable modes to pass 1-halogeno-3,3,3-trifluoropropene through a reactor loaded with a catalyst heated at 100° C. to 350° C. with a contact time of 1 to 300 seconds.

In the reaction according to the present invention, pressure is not particularly limited. That is, it is possible to conduct that at a pressure lower than atmospheric pressure, under atmospheric pressure, or higher than atmospheric pressure. In general, pressure under atmospheric pressure is preferable.

The reaction according to the present invention can be conducted even in the presence of an inert gas, such as nitrogen or argon, stable in the reaction according to the present invention.

The chlorination-dehydrohalogenation reaction according to the present invention is conducted in a gas phase by using a general chemical engineering apparatus and is conducted by introducing 1-halogeno-3,3,3-trifluoropropene and chlorine into a reaction region loaded with a catalyst having an adjusted temperature. The reactor is normally tubular. There is used a material resistant against hydrogen chloride, for the reaction tube, the related raw material introducing system, the outflow system, and the related units. The material can be exemplified as typical ones particularly by stainless steel, such as austenite type, or high nickel alloys, such as Monel™, Hastelloy™ and Inconel™, and copper-clad steel. It is, however, not limited to these. The reactor may be a void column. It is, however, optional to use a loading of the above-mentioned material in order to improve the heat exchange efficiency.

The method for purifying 1,2-dichloro-3,3,3-trifluoropropene from the reaction product obtained by the reaction according to the present invention is not particularly limited. It is possible to use a publicly-known purification method. It is possible to obtain a high-purity 1,2-dichloro-3,3,3-trifluoropropene, for example, by passing the reaction product through a cooled condenser for condensation, a washing with water and/or an alkali solution to remove chlorine component, acid, etc., a drying with a desiccant, such as zeolite and activated carbon, and then a normal distillation operation. In case that 1-halogeno-3,3,3-trifluoropropene exists as the unreacted raw material in the reaction product, it is possible to separate and recover 1-halogeno-3,3,3-trifluoropropene from the reaction product by a normal distillation operation. The separated 1-halogeno-3,3,3-trifluoropropene can be used again as the raw material of the reaction according to the present invention.

1,2-dichloro-3,3,3-trifluoropropene obtained by the production process according to the present invention exists as a liquid under ordinary temperature and ordinary pressure. 1,2-dichloro-3,3,3-trifluoropropene to be produced is obtained as a mixture of cis and trans stereoisomers, but these stereoisomers can be separated by a purification operation, such as distillation. With this, it is possible to obtain high-purity cis-1,2-dichloro-3,3,3-trifluoropropene and trans-1,2-dichloro-3,3,3-trifluoropropene.

In the following, the present invention is explained in detail by examples, but the present invention is not limited to these examples.

PREPARATION EXAMPLE 1

Preparation of Antimony/Activated Carbon

A cylindrical, stainless steel (SUS316L) reaction tube, which was equipped with an electric furnace and had an inner diameter of 2.7 cm and a length of 40 cm, was loaded with 50 ml of a catalyst in which 48 mass % of antimony pentachloride had been supported on a dry activated carbon (GRANULAR SHIRO SAGI G2X: 4/6-1 made by Japan EnviroChemicals, Ltd.), followed by increasing the temperature until 150° C. for sintering while allowing nitrogen to flow at a flow rate of 20-30 ml/min. to prepare a catalyst.

PREPARATION EXAMPLE 2

Preparation of Chromium/Activated Carbon

A 40 mass % $CrCl_3$ aqueous solution as a commercial reagent was diluted to prepare a 20 mass % aqueous solution. 100 g of a granular activated carbon (Japan EnviroChemicals, Ltd., GRANULAR SHIRO SAGI G2X) was immersed in 156 g of the previously prepared 20 mass % $CrCl_3$ aqueous solution, followed by standing still for one day and one night. Then, the activated carbon was taken out by filtration, followed by maintaining at 100° C. in a hot-air circulating dryer for drying further one day and one night.

A cylindrical, stainless steel (SUS316L) reaction tube, which was equipped with an electric furnace and had an inner diameter of 2.7 cm and a length of 40 cm, was loaded with 50 ml of the obtained chromium-supported catalyst, followed by increasing the temperature until 300° C. while allowing nitrogen gas to flow. At the point when discharge of water was not found, nitrogen gas was accompanied with hydrogen fluoride, and its concentration was gradually increased. The condition was maintained for one hour to prepare a catalyst.

PREPARATION EXAMPLE 3

Preparation of Fluorinated Alumina

A cylindrical, stainless steel (SUS316L) reaction tube, which was equipped with an electric furnace and had an inner diameter of 2.7 cm and a length of 40 cm, was loaded with 50 ml of a granular γ-alumina catalyst (SUMIKA ALCHEM CO., LTD., KHS-46), followed by increasing the temperature until 200° C. while allowing nitrogen gas to flow. At the point when discharge of water was not found, nitrogen gas was accompanied with hydrogen fluoride (HF), and its concentration was gradually increased. When hot spot resulting from fluorination of the loaded alumina reached the exit end of the reaction tube, the temperature of the reactor was increased to 300° C. The condition was maintained for one hour to prepare a catalyst.

EXAMPLE 1

Catalyst: Activated Carbon

A cylindrical, stainless steel (SUS316L) reaction tube, which was equipped with an electric furnace and had an inner diameter of 2.7 cm and a length of 40 cm, was loaded with 50 ml of a previously dried, granular activated carbon (SHIRO SAGI G2X: made by Japan EnviroChemicals, Ltd.), followed by increasing the temperature while allowing nitrogen to flow at a rate of 10 ml/min. When the temperature of the reaction tube reached 150° C., 1-chloro-3,3,3-trifluoropropene was vaporized, followed by supplying it at a flow rate of about 0.29 g/min and chlorine at a flow rate of about 0.16 g/min (the molar ratio of 1:1, a contact time of about 30 seconds). When the flow rates became stable, the nitrogen supply was stopped. The product gas flowing out of the reactor was passed through a gas washing bottle containing a 10 mass % NaOH aqueous solution cooled in an iced water bath to absorb the unreacted chlorine and hydrogen chloride and collect the reaction product. As the collected reaction product was analyzed by a gas chromatograph, yield of 1,2-dichloro-3,3,3-trifluoropropene (HCFC-1223xd) was 30.3%. Yield referred to herein represents yield determined by gas chromatography (It may be referred to as "GC yield". It is the same in the following). It is yield determined with no isolation of the target compound.

EXAMPLE 2

Catalyst: Antimony/Activated Carbon

The reaction was conducted similar to Example 1, except in that 50 ml of the catalyst prepared by Preparation Example 1 was used. As a result, yield of 1,2-dichloro-3,3,3-trifluoropropene was 46.4%. Yield referred to herein represents GC yield.

EXAMPLE 3

Catalyst: Chromium/Activated Carbon

The reaction was conducted similar to Example 1, except in that 50 ml of the catalyst prepared by Preparation Example 2 was used. As a result, yield of 1,2-dichloro-3,3,3-trifluoropropene was 45.3%. Yield referred to herein represents GC yield.

EXAMPLE 4

Catalyst: Fluorinated Alumina

The reaction was conducted similar to Example 1, except in that 50 ml of the catalyst prepared by Preparation Example 3 was used. As a result, yield of 1,2-dichloro-3,3,3-trifluoropropene was 35.2%. Yield referred to herein represents GC yield.

EXAMPLE 5

2282 g of a cis-trans isomer mixture of 1223zd (78.18% trans-1,2-dichloro-3,3,3-trifluoropropene and 16.19% cis-1,2-dichloro-3,3,3-trifluoropropene) was purified by a glass precision distillation apparatus, thereby obtaining 1587 g of trans-1,2-dichloro-3,3,3-trifluoropropene with a purity of 99.97%.

REFERENCE EXAMPLE 1

A 1000 ml glass reactor equipped with a gas inlet was cooled in an iced water bath of 0° C. It was charged with 554.1 g (4.24 mol) of trans-1-chloro-3,3,3-trifluoropropene. While cooling in the iced water bath of 0° C., chlorine was introduced into the reactor at 0.83 g/min. It was irradiated with light by a high-pressure mercury lamp from the outside of the reactor. The raw material organic matter and chlorine in the reactor were stirred by a magnetic stirrer. After the introduction of chlorine for 6 hours, the light irradiation of the high-pressure mercury lamp was stopped, and the reaction was terminated. After the reaction, the organic matter in the reactor was washed with water, a weakly alkali aqueous solution, and saturated brine, thereby obtaining 836.3 g of a composition containing 1,1,2-trichloro-3,3,3-trifluoropropane (HCFC-233da).

As the obtained composition was analyzed by a gas chromatograph, the composition was found to contain 96.2% 1,1,2-trichloro-3,3,3-trifluoropropane. Yield of 1,1,2-trichloro-3,3,3-trifluoropropane was 94.1%. Herein, "%" of the value of the compositional analysis represents "a real %" of the composition obtained by measuring the reaction product by gas chromatography (unless particularly described, the detector is FID).

The invention claimed is:

1. A process for producing 1,2-dichloro-3,3,3-trifluoropropene, comprising reacting a 1 halogeno-3,3,3-trifluoropropene represented by the general formula [1]:

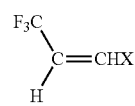

[1]

with chlorine in a gas phase in the presence of a catalyst;
wherein X represents a fluorine atom, chlorine atom or bromine atom.

2. The process according to claim 1, wherein the 1-halogeno-3,3,3-trifluoropropene and the chlorine are brought into contact with the catalyst with a contact time of from 1 second to 300 seconds at a reaction temperature of from 100° C. to 350° C.

3. The process according to claim 1, wherein the 1-halogeno-3,3,3-trifluoropropene is 1-chloro-3,3,3-trifluoropropene.

4. The process according to claim 1, wherein the catalyst is a metal compound containing at least one metal selected from the group consisting of aluminum, chromium, titanium, manganese, iron, nickel, cobalt, copper, magnesium, zirconium, molybdenum, zinc, tin, lanthanum, and antimony.

5. The process according to claim 4, wherein the metal compound is a metal fluoride.

6. The process according to claim 4, wherein the metal compound is a fluorinated alumina or a fluorinated chromia.

7. The process according to claim 1, wherein the catalyst is a supported catalyst in which a metal compound containing at least one metal selected from the group consisting of aluminum, chromium, titanium, manganese, iron, nickel, cobalt, copper, magnesium, zirconium, molybdenum, zinc, tin, lanthanum, and antimony is supported on carbon.

8. The process according to claim 7, wherein the metal compound is a metal fluoride.

9. The process according to claim 7, wherein the catalyst is an antimony-supported activated carbon or a chromium-supported activated carbon.

10. The process according to claim 1, wherein the catalyst is activated carbon.

11. A process for producing a high-purity 1,2-dichloro-3,3,3-trifluoropropene, wherein the 1,2-dichloro-3,3,3-trifluoropropene obtained by the process according to claim 1 is further purified.

12. A process for producing 1,2-dichloro-3,3,3-trifluoropropene, wherein the 1-halogeno-3,3,3-trifluoropropene separated from the 1,2-dichloro-3,3,3-trifluoropropene by the process according to claim 11 is recovered.

13. A process for producing 1,2-dichloro-3,3,3-trifluoropropene, wherein the 1-halogeno-3,3,3-trifluoropropene separated from the 1,2-dichloro-3,3,3-trifluoropropene by the process according to claim 11 is used again as the raw material.

14. A process for producing trans-1,2-dichloro-3,3,3-trifluoropropene, wherein the 1,2-dichloro-3,3,3-trifluoropropene obtained by the process according to claim 1 is further purified.

15. A process for producing cis-1,2-dichloro-3,3,3-trifluoropropene, wherein the 1,2-dichloro-3,3,3-trifluoropropene obtained by the process according to claim 1 is further purified.

* * * * *